United States Patent [19]
Geerts et al.

[11] Patent Number: 6,005,061
[45] Date of Patent: Dec. 21, 1999

[54] ORGANO-ALUMINOXY PRODUCT AND USE

[76] Inventors: Rolf L. Geerts, 4610 SE Barlow Dr., Bartlesville, Okla. 74006; Tara G. Hill, 60 Clubhouse La., Apt. C, Fairfield, Ohio 45014; Scott E. Kufeld, 4743 Melody La., Bartlesville, Okla. 74006

[21] Appl. No.: 08/373,129

[22] Filed: Jan. 17, 1995

Related U.S. Application Data

[62] Division of application No. 08/017,207, Feb. 12, 1993, Pat. No. 5,411,925.

[51] Int. Cl.$^6$ .................................................. C08F 2/06
[52] U.S. Cl. ............................ 526/64; 526/132; 526/153; 526/160; 526/348.5; 526/351; 526/352; 502/152; 502/153
[58] Field of Search .............................. 526/64, 132, 153, 526/160

[56] References Cited

U.S. PATENT DOCUMENTS 5,001,244  3/1991  Welburn, Jr. ............................... 556/53

*Primary Examiner*—David W. Wu
*Attorney, Agent, or Firm*—Edward L. Bowman

[57] ABSTRACT

In accordance with the present invention there is provided a new solid aluminoxy composition prepared by reacting aluminoxane with a boroxine. Still further there is provided olefin polymerization catalyst systems incorporating the inventive solid aluminoxy composition. Still further, there is provided processes of polymerization using the inventive solid aluminoxy composition.

15 Claims, 4 Drawing Sheets

ORGANO-ALUMINOXY PRODUCT AND USE

This application is a Division of application Ser. No. 08/017,207, filed Feb. 12, 1993, now U.S. Pat. No. 5,411, 925.

FIELD OF THE INVENTION

The present invention relates to aluminoxy products. The term organo-aluminoxy as used herein refers to organic compounds having a plurality of aluminum atoms each bound to at least two oxygen atoms. In another aspect, the present invention relates to a method of modifying organic aluminoxanes to make them suitable for use in particle form polymerization. In still another aspect, the present invention relates to a metallocene catalyst comprising a modified organic aluminoxane. In still another aspect, the present invention relates to a process for polymerizing olefins using the modified organic aluminoxane.

BACKGROUND OF THE INVENTION

Organic aluminoxanes are one form of aluminoxy compound. Organic aluminoxanes can be produced by the partial hydrolysis of hydrocarbyl aluminum compounds. Such aluminoxanes have been found useful in a variety of chemical reactions, including utility as catalyst components for polymerization catalysts, especially in high activity metallocene catalyst systems.

The combination of such aluminoxanes with metallocenes has been shown to be useful for certain types of olefin polymerization. One of the earliest patents containing such a disclosure is U.S. Pat. No. 3,242,099, the disclosure of which is incorporated herein by reference. Such metallocene catalysts have been used in homogeneous solution polymerization. Since such homogeneous catalyst systems are soluble in the polymerization medium it is generally observed that the resulting polymer has low bulk density.

Further, attempts to use metallocene/aluminoxane catalysts in a slurry or particle form type polymerization have not heretofore been found to be commercially feasible. In slurry or particle form polymerization, the polymerization conditions are selected such that the polymer forms as discrete particles which are insoluble in the polymerization reaction medium during the polymerization. It has been observed that when such particle form polymerizations are carried out in the presence of a metallocene/aluminoxane catalyst system, large amounts of polymeric material are formed on the surfaces of the polymerization vessel. This fouling is particularly detrimental in a particle form process since it produces an adverse effect on the heat transfer and also results in the need for periodic if not continuous cleaning of the reactor. In order to have a metallocene/aluminoxane catalyst useful in a commercial continuous particle form process such as those using a loop reactor, it is necessary to have a catalyst system which will not cause significant amounts of reactor fouling.

It is known that a solid form of aluminoxane can be obtained by treating a commercial organo aluminoxane solution with a countersolvent; however, even that solid has been found to cause reactor fouling in slurry polymerizations. Even when a countersolvent is used to precipitate the aluminoxane onto an insoluble particulate carrier reactor fouling is still a problem in slurry, i.e. particle form polymerization.

An object of the present invention is to provide a new organo-aluminoxy composition which while still active as a cocatalyst for a transition metal polymerization catalyst, at the same time does not produce significant reactor fouling in a particle form process.

Another aspect of the present invention relates to a method for making this new organo-aluminoxy composition.

Still another aspect of the present invention relates to polymerization catalyst systems comprising a transition metal compound and the new organo-aluminoxy composition.

Still yet another aspect is to provide a solid organo-aluminoxy composition having a surface area greater than that of the solid resulting from the vacuum stripping of an aluminoxane solution. Inventive solids having a surface area as high as 300 m$^2$/g as determined by a BET test have been prepared.

Another object is to provide a stable solid metallocene polymerization catalyst comprising the combination of a metallocene and the inventive solid aluminoxane.

Still yet another aspect of the present invention relates to the polymerization of olefins using the new organo-aluminoxy composition as the cocatalyst, especially in particle form polymerizations.

Other aspects, objects and advantages of the present invention will become apparent to those skilled in the art having the benefit of the following disclosure.

SUMMARY OF THE INVENTION

In accordance with the present invention a solid organo-aluminoxy product is produced by reacting an organic aluminoxane with an organic boroxine selected from the group consisting of organo boroxines.

In accordance with another aspect of the present invention a catalyst system suitable for the polymerization of olefins is produced by combining the new organo-aluminoxy composition with a transition metal based olefin polymerization catalyst.

Still another object of the present invention is to provide a relatively stable solid olefin polymerization catalyst comprising a metallocene and the inventive solid aluminoxy composition.

In accordance with still another aspect of the present invention there is provided a process for producing polyolefins comprising contacting at least one olefin under suitable conditions with a catalyst system comprising a suitable catalyst and the inventive organo-aluminoxy composition.

In accordance with still another aspect of the invention there is provided the new organo-aluminoxy composition resulting from the reaction of aluminoxane with the boroxine.

DETAILED DESCRIPTION OF THE INVENTION

In accordance with the present invention, organic aluminoxanes are modified to produce a new organo-aluminoxy composition that can be used as a cocatalyst in a particle form polymerization without causing significant fouling of the polymerization reaction vessel.

Various techniques are known for making organic aluminoxanes. One technique involves the controlled addition of water to a trialkylaluminum. Another technique involves combining a trialkylaluminum and a hydrocarbon with a compound containing water of adsorption or a salt containing water of crystallization. The present invention is considered applicable to any of the commercially available organic aluminoxanes that are soluble in a hydrocarbon.

The exact structure of organic aluminoxanes is often the subject of much discussion between scholars. It is generally accepted that the aluminoxanes are oligomeric, linear and/or cyclic hydrocarbyl aluminoxanes having repeating units of the formula Typically the linear aluminoxanes are said to contain oligomers of the formula:

The oligomeric, cyclic aluminoxanes are generally viewed as having the formula:

In the above formulas, R is a hydrocarbyl group, typically a $C_1$–$C_8$ alkyl group, and n is typically 2 to 50, preferably 4 to 40, m is typically 3 to 50, preferably 4 to 40. Generally, the aluminoxanes are more active as polymerization catalysts when m and n are greater than 4, more preferably at least about 10. Typically in the aluminoxanes used in the polymerization of olefins R is predominantly methyl or ethyl. Preferably at least about 30 mole percent of the repeating groups have an R which is methyl, more preferably at least 50 mole percent, and still more preferably at least 70 mole percent of the repeating units have methyl as the the R group.

Some experts believe that the resulting oligomeric aluminoxane products have some significant amounts of unreacted yet somehow strongly bonded trialkylaluminums associated therewith. Among some researchers there has even been the theory that perhaps the trialkylaluminums associated with the aluminoxane is actually the material which causes the aluminoxane to be effective as a cocatalyst with metallocenes and other transition metal olefin polymerization catalysts. See L. Resconi et al, *Macromolecules,* 1990 (23), 4489–4491.

It is considered that the present invention can be applied to any of the above discussed aluminoxanes. Aluminoxanes are generally obtained commercially in the form of hydrocarbon solutions, generally aromatic hydrocarbon solutions, since the more active higher molecular weight aluminoxanes are generally insoluble in aliphatic hydrocarbons. Unless these samples have been subjected to special treatment, they typically contain trialkylaluminum as well as the oligomeric aluminoxane. The trialkyl aluminums generally include those in which the alkyl groups contain 1 to 8 carbon atoms, most generally, one to two carbon atoms.

The present invention is particularly useful for modifying aluminoxane solutions containing both trialkylaluminums and aluminoxanes, particularly the aluminoxanes wherein n of the above formula is at least about 2 and m is at least about 3, and even more preferably wherein n and m are both greater than 4. The preferred aluminoxanes for use in the present invention are those in which R of the above formulas is methyl or ethyl, preferably methyl.

Various boroxines are known in the art. The term organo boroxine as used herein refers to compounds of the formula $(RBO)_3$ wherein each R is the same or a different organo group free of hydroxyl (HO—) or mercapto (HS—) groups. The R groups could include such radicals as methyl, ethyl, isopropyl, tertiary butyl, 2-ethyl ethylene, tri-n-butyl methyl, o-tolyl, phenyl, o-tri-fluoro methyl phenyl, o-chloro-phenyl, 2,6-dimethyl phenyl, $C_2H_5$—S—$CH_2CH_2CH_2$—, $CH_2$=CH—$CH_2$—, α-naphthyl, β-naphthyl, and the like. The R groups could also be R'O—, R'S—, R'$_2$N—, R'$_2$P—, and R$_3$'Si— wherein each R' is a hydrocarbyl group. Generally each R group contains about 1 to about 25 carbon atoms, more typically 1 to 10 carbon atoms. Especially preferred are the hydrocarbyl boroxines and the hydrocarbyl oxy boroxines. Examples of hydrocarbyl boroxines include trimethyl boroxine, triethyl boroxine, tri-n-propyl boroxine, tributyl boroxine, tricyclohexyl boroxine, triphenyl boroxine, methyl diethyl boroxine, dimethylethyl boroxine, and the like. The currently preferred hydrocarbyl boroxines are trimethyl boroxine and triethyl boroxine. The term hydrocarbyloxy boroxine refers to compounds of the formula $((R'O)BO)_3$ wherein each R' can be the same or different hydrocarbyl group, generally containing about 1 to about 10 carbon atoms. Trialkyloxy boroxines are currently preferred. Trimethoxy boroxine is an example.

The reaction of the boroxine with the aluminoxane can be carried out in any suitable manner. One particularly desirable technique simply involves contacting the two reactants in a suitable liquid diluent. One preferred technique involves contacting a hydrocarbon solution of the aluminoxane with a hydrocarbon solution of the boroxine. Another technique involves contacting a hydrocarbon solution of the aluminoxane with a countersolvent to produce a slurry comprising soluble aluminoxane and insoluble particulate aluminoxane and then contacting the resulting slurry with a solution of the boroxine. It is also within the scope of the present invention to carry out the reaction of the boroxine and the aluminoxane in the presence of a particulate diluent so that the insoluble product becomes deposited upon the particulate diluent. Typical particulate diluents would include such inorganic materials as silica, alumina, aluminum phosphate, silica-alumina, titania, kaolin, fumed silica, and the like.

It is also within the scope of the present invention to prepare the inventive particulate organo-aluminoxy composition and then combine it with a solution of a trialkylaluminim compound, e.g. trimethylaluminum or others of the type mentioned above, and then to contact the resulting slurry with additional boroxine of the type described above. It is believed that this process may provide a method for further increasing the molecular weight of the particulate aluminoxy composition that is initially produced by reacting the aluminoxane with the boroxine. Obviously, such a process could be repeated several times to obtain the desired level of molecular weight, particle size, bulk density, or other characteristic that is desired for a particular application.

The amount of boroxine employed relative to the aluminoxane can vary over a wide range depending upon the particular results desired. A technique which has been used in this invention for reflecting the ratio of boroxine to aluminoxane, involves the use of a calculated amount for the amount of aluminoxy aluminum in the aluminoxane solution. As used herein the term calculated aluminum is the value obtained by using a vacuum to strip the solvent off a known volume of the aluminoxane solution; weighing the recovered solid; and dividing the weight of the solid per milliter by the average molecular weight of the aluminoxy units, i.e. 58 for methylaluminoxane, so that one obtains a calculated value for the number of moles of aluminum per volume of the aluminoxane solution that is to be reacted with the boroxine. It is theorized that a substantial portion of any free trihydrocarbyl aluminum in the aluminoxane solution is removed when the solvent is stripped off. Any trihydrocarbyl aluminum that is present in the solid recovered after the vacuum stripping, is not considered to have a significant effect upon the calculated aluminum value. Using this method, the atomic ratio of the boron in the boroxine to calculated Al in the aluminoxy units of the aluminoxane employed will be in the range of about 1/20 to about 1/3, more preferably about 1/15 to about 1/5, still more preferably about 1/7. As noted above, the commercial aluminoxane solutions generally contain at least some trihydrocarbyl aluminum, in addition to aluminoxy units. Generally, the trihydrocarbyl aluminum accounts for about about 0.1 to about 35 weight percent of the aluminum in the solution. It is generally preferred for the boroxine to be employed in such an amount that the molar ratio of the boroxine to the trihydrocarbyl aluminum be at least about 0.3334/1.

In view of the demonstrated activity of the boroxine precipitated organo aluminoxy products of the present invention, it is considered that such solid organo aluminoxy products will be suitable as replacements for soluble aluminoxy products in polymerization reactions. Accordingly, the inventive solid aluminoxanes should be suitable as catalyst components with any number of the transition metal-containing olefin polymerization catalysts that have in the past been employed with soluble aluminoxanes. Some examples of such transition metal-containing catalysts are disclosed in the previously mentioned U.S. Pat. No. 3,242, 099, the disclosure of which is incorporated herein by reference. The use of more than one such catalyst is also within the scope of the present invention. In a preferred embodiment, the catalyst portion of the catalyst system is selected from transition metal compounds of metals of Groups IVB, VB, and VIB. Examples of the transition metals thus include zirconium, titanium, hafnium, and vanadium. Such compounds can be represented by the formula $MX_n$ wherein M represents the transition metal atom and X represents a halogen atom or an organo group, and n is the valence state of the transition metal. Some illustrative examples of such transition metal compounds include vanadium dichloride, vanadium trichloride, vanadium tetrachloride, vanadium pentafluoride, vanadium triiodide, titanium dibromide, titanium tetrachloride, titanium trichloride, titanium tetrafluoride, titanium tetraiodide, titanium tetrabromide, zirconium trichloride, zirconium tetrachloride, chromic chloride, titanium tetraethoxide, titanium tetrabutoxide, zirconium tetrabutoxide, dicyclopentadienyl titanium dichloride, dicyclopentadienyl zirconium dichloride, chromium (III) 2-ethylhexanoate, and the like.

In a particular preferred embodiment the transition metal catalyst component comprises a metallocene. Examples of metallocenes include compounds of the formula $ML_x$ wherein M is the transition metal, at least one L is a ligand coordinated to the transition metal compound having an alkyldienyl skeleton, the other L's can be selected from ligands having alkyldienyl skeletons, hydrocarbon radicals having 1 to 12 carbon atoms, alkoxy radicals having 1 to 12 carbon atoms, aryl oxy radicals having 6 to 12 carbon atoms, halogen, or hydrogen, and x is the valence of the transition metal.

The term "alkyldienyl skeleton" is intended to include such ligands as cyclopentadienyl, alkyl-substituted cyclopentadienyl compounds such as methyl cyclopentadienyl, ethyl cyclopentadienyl, n-butyl cyclopentadienyl, dimethyl cyclopentadienyl, pentamethyl cyclopentadienyl, and the like. Other examples of such cycloalkyldienyl ligands include substituted and unsubstituted indenyls or fluorenyls, tetrahydroindenyls, and the like. Examples of such metallocenes are disclosed in U.S. Pat. No. 5,091,352, the disclosure of which is incorporated herein by reference. Some specific examples include bis cyclopentadienyl zirconium dichloride, bis(methylcyclopentadienyl) zirconium dichloride, and bis(n-butyl cyclopentadienyl) zirconium dichloride.

It is also within the scope of the present invention to have two of the L groups be cycloalkyldienyl-type groups which are bonded together by a suitable bridging group. Some such metallocenes are referred to in the art as sandwich-bonded metallocenes. The term "sandwich-bonded metallocenes" is used to indicate that the metal of the metallocene is sandwiched between two opposed cycloalkyldienyl portions of the bridged ligand. Some examples of such bridged ligands include 1-(9-fluorenyl)-1-(cyclopentadienyl) methane, fluorenyl cyclopentadienyl dimethyl methane, 1,2-bis-indenyl ethane, and the like. Metallocenes also include so-called "half-sandwich-bonded", i.e. those in which only one of the cycloalkyldienyl portions is bonded to the metal. An example would be (1-fluorenyl-1-cyclopentadienyl methane) zirconium trichloride.

It is also within the scope of the present invention to employ the inventive solid aluminoxy product in combination with the third generation supported high activity transition metal containing olefin polymerization catalysts. Some examples of typical high activity solid transition metal containing olefin polymerization catalysts include those disclosed in U.S. Pat. Nos. 4,326,988 and 4,394,291, the disclosures of which are incorporated herein by reference.

It is also within the scope of the invention to prepare a prepolymerized solid catalyst composition by combining the transition metal component and the inventive solid aluminoxy composition and conducting prepolymerization of an olefin to produce an active prepolymerized solid which is later used in a polymerization zone.

The particular polymerization conditions employed using the inventive compositions can vary depending upon the particular results desired. It is considered that the inventive solid organo aluminoxy product can be employed in solution, suspension, and gas phase polymerization of a wide range of olefinically unsaturated monomers. The ratio of the transition metal catalyst to the inventive solid aluminoxy product can vary widely depending upon the particular catalyst selected and the results desired. Typically, the atomic ratio of aluminum in the inventive aluminoxy product to the transition metal is in the range of about 1/1 to about 5000/1, preferably about 15/1 to about 1000/1, and more preferably about 100/1 to about 1000/1. For a particular transition metal catalyst it is considered that polymerizations can be carried out under the same conditions as would be suitable for prior art aluminoxanes.

Examples of some monomers for polymerization include ethylene and alpha-olefins having 3 to 20 carbon atoms, such as propylene, 1-butene, 1-hexene, 4-methyl-1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, feed, catalyst, and diluent, if employed, are continuously added to the reactor as needed and polymer product is continuously or at least periodically removed.

The inventive organo aluminoxy product has been demonstrated to be effective as a cocatalyst in the continuous loop slurry type polymerization with metallocene catalysts for the production of polyethylenes having a broad range of properties. Generally in such processes, ethylene is polymerized in the presence of a suitable liquid diluent, a higher alpha-olefin comonomer, and optionally, hydrogen. The polymerization temperature can vary over the range which will allow for slurry polymerization. Often the slurry polymerization would be conducted at a temperature in the range of about 60° C. to about 100° C., although higher and lower temperature can be used. The employment of hydrogen in such a continuous loop polymerization using the inventive cocatalyst has been demonstrated to provide very interesting effects, specifically, broad molecular weight distribution. Polyethylenes of broader molecular weight distribution are produced by introducing only enough hydrogen to produce the desired melt index without reducing the molecular weight distribution. This is particularly surprising in that in the past, metallocene polymerizations employing a single metallocene catalyst have generally given narrow molecular weight distribution products, for example products having a molecular weight distribution in which the ratio of the weight average molecular weight to the number average molecular weight is in the range of about 2 to 3. In contrast, by using the correct conditions with the inventive solid aluminoxy product, it is possible in a slurry polymerization to produce polyethylene in which the ratio of the weight average molecular weight to the number average molecular weight is as high as 21 or more.

A further understanding of the present invention and its objects and advantages will be provided by referring to the following examples.

EXAMPLE I

Figure 1:
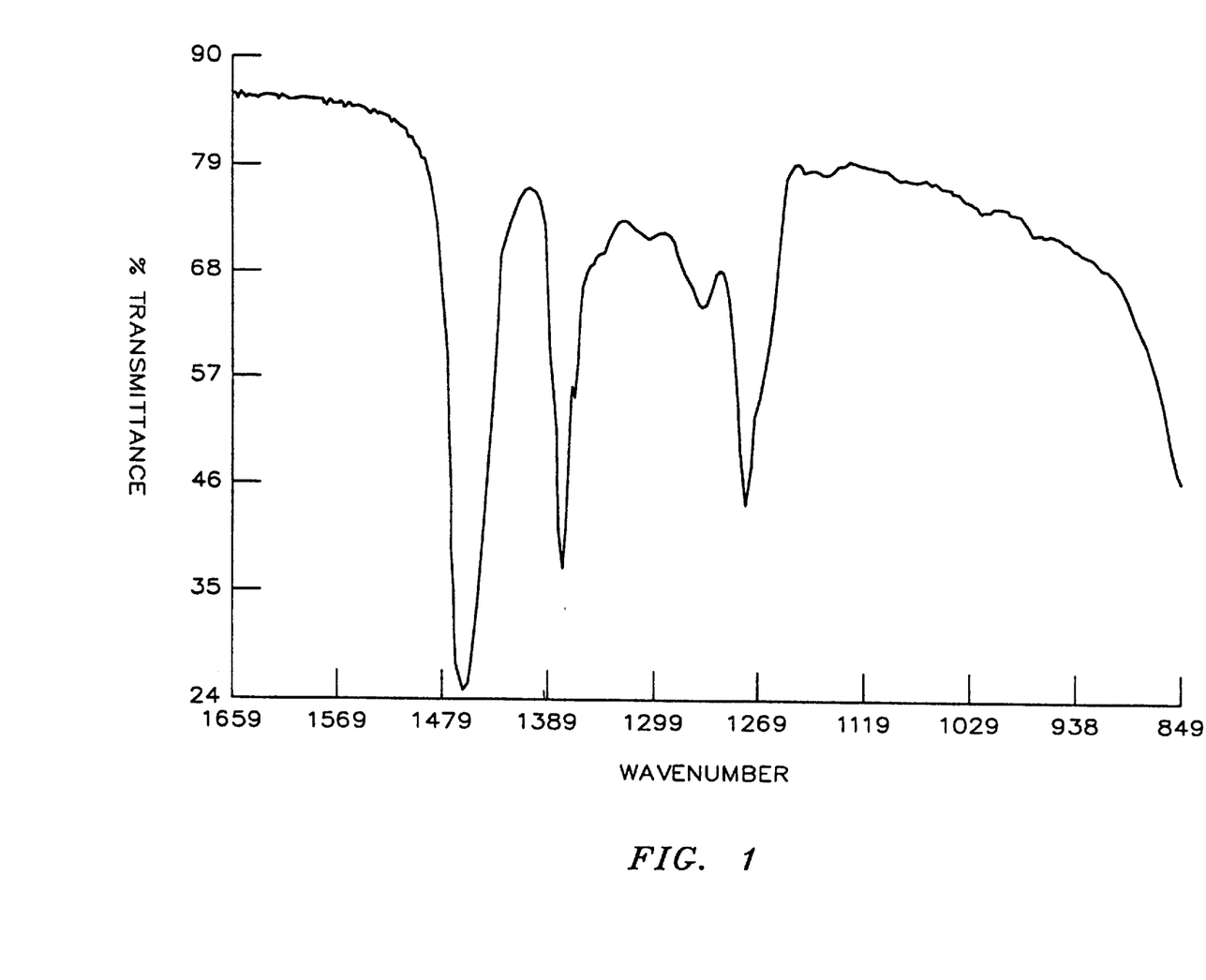
FIG. 1 is a graph showing an IR spectrum of the solid resulting when the solvent is vacuum stripped from a commercial methylaluminoxane solution.
Figure 2:
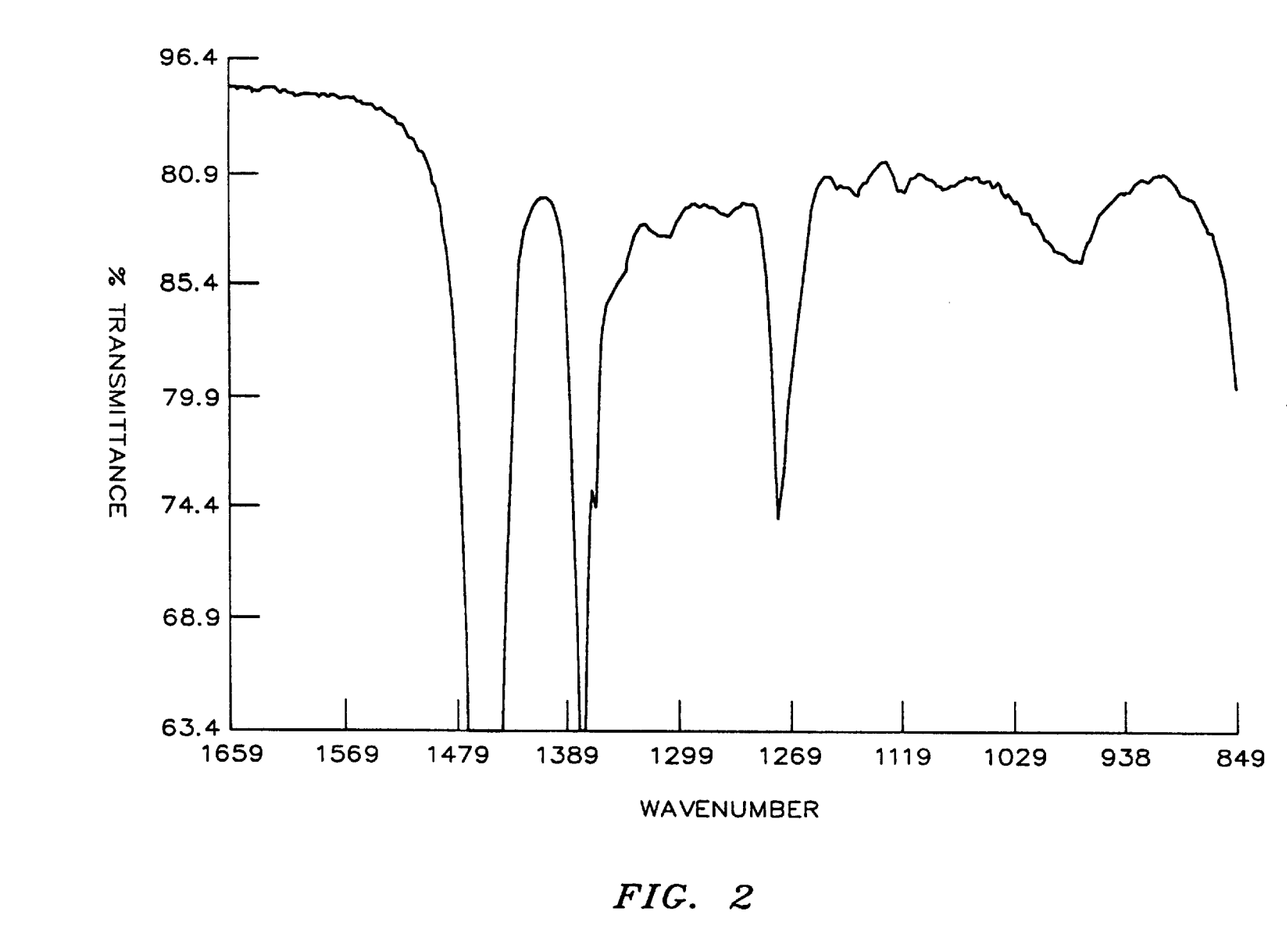
FIG. 2 is a graph showing an IR spectrum of a solid produced by reacting a commercial methylaluminoxane solution with methoxy boroxine.

A toluene solution of methylaluminoxane obtained from Schering was reported to contain about 30 weight percent of methylaluminoxane (herein also referred to as MAO) based on a total weight of the solution. Drying a 2 ml portion of that commercial solution in vacuo at room temperature yielded 0.57 grams of solid. FIG. 1 shows the infrared spectrum of such a solid in nujol.

While being stirred, a 20 ml portion of the Schering 30 weight percent MAO/toluene solution had about 50 ml of decane added. The decane had been dried over molecular sieves. The resulting mixture was cloudy. It was removed from the dry box and evacuated. The solution was stirred at 35° C. for 3 hrs. under a vacuum. The white slurry was returned to the dry box and filtered and then the solids were dried in vacuo. A yield of 2.69 grams of a colorless solid was obtained. It is thus estimated that more than half of the methylaluminoxane remained in the liquid. The inventors theorize that this decane soluble MAO may have been responsible for at least some of the adverse effects that were noted when an attempt was made to carry out a metallocene catalyzed ethylene polymerization under particle form conditions using the commercial MAO.

Then 0.1 gram of methylboroxine was dissolved in 1 ml of toluene. The resulting toluene solution was added dropwise to a 20 ml aliquot of the filtrate, i.e. the decane soluble MAO. Immediately upon addition of the methylboroxine solution, copious white solids appeared. After stirring for 1 hr. the solids were collected on a filter, washed with 10 ml of hexanes and dried. About 0.47 grams of solids were recovered.

A 0.23 gram portion of the solids produced from the methylboroxine reaction was slurried in 5 ml of decane. Then 10 mg of bis(cyclopentadienyl)zirconium dichloride was dissolved in 1 ml of toluene and the resulting solution was added to the decane slurry. The slurry was stirred for 1 hr. and yielded a brown solid phase and a colorless solution phase. The solid phase is referred to herein as Catalyst System A.

The resulting solid metallocene catalyst system was then evaluated for activity in the polymerization of ethylene under particle form conditions. The polymerization was conducted at about 70° C. in 2 liters of isobutane in the presence of hydrogen in an autoclave reactor. The partial pressure of the isobutane and hydrogen was about 175 psi and the partial pressure of the ethylene was about 380 psi. The polymerization was carried out for 1 hr. and yielded 224.4 grams of dry polymer having a melt index of 0.48 and a high load melt index of 10.28. The bulk density was 23.4 gms/100 ml. The reactor was easy to clean up. There was minimal fouling or coating of polymer on the reactor. The fouling observed with Catalyst System A was significantly less than that observed when a similar polymerization was carried out using the same metallocene with the commercial MAO/toluene as a cocatalyst.

EXAMPLE II

In this case, a methylaluminoxane obtained from Ethyl Corporation was evaluated. The methylaluminoxane product was a solution in toluene. The weight percent MAO in the toluene solution was reported by the manufacturer to be about 10 weight percent. The product was also reported to have an aluminum content of about 4.2 weight percent. About 22 weight percent of the aluminum was reported as being considered to be present as trimethylaluminum.

While 10 ml of the commercial MAO/toluene solution was stirred, 25 ml of hexane was added by a syringe. The previously clear toluene solution became cloudy. The slurry was stirred for 1 hr. at 25° C. in a dry box. The solids were collected on a filter and dried. About 0.142 grams of solid was recovered which is considered to be about 15 weight percent of the methylaluminoxane in the original slurry.

The resulting solid methylaluminoxane was added to 10 ml of mixed hexanes and then a solution formed by adding 4 milligrams of bis(cyclopentadienyl)zirconium dichloride to toluene was combined with the hexane slurry. The solid turned pale yellow.

This catalyst was then evaluated for the particle form polymerization of ethylene using conditions of the type described for Example I. The 1 hr. polymerization yielded 235.3 grams of dry polymer. The polymer had fairly good particle form but the reactor had significant fouling and was hard to clean up. A hot wash with toluene was required to remove material coating the reactor. This demonstrates that even though countersolvent precipitation resulted in a solid product, that product still resulted in reactor fouling.

EXAMPLE III

An experiment was carried out by adding 25 ml of hexane to 10 ml of the same commercial Ethyl Corporation toluene solution of methylaluminoxane used in Example II. A precipitate formed. Then 2 ml of a hexane solution containing 0.034 grams of methylboroxine was added to the slurry. The slurry was stirred for 1 hr. at 25° C. in a dry box. The solids were collected on a filter and dried. The yield was 0.221 grams which is calculated to be about 22.5 weight percent of the MAO in the commercial solution.

To the filtrate was added 0.4 grams methylboroxine in 2 ml of hexane with vigorous stirring. The solution fumed slightly and copious precipitates were evident. The slurry was stirred for 1 hr. and the solids were collected on a filter. The recovered dried solids weighed 0.55 grams. This is considered to correspond to about 55.8 weight percent of the total MAO in the commercial solution.

A first catalyst, referred to herein as Catalyst B, was prepared from the solid obtained from the initial precipitation of the commercial MAO solution with methylboroxine. That catalyst preparation involved slurrying 0.221 grams of the boroxine precipitated MAO in 10 ml of hexane and then adding 3 ml of a toluene solution containing 6 milligrams of bis(cyclopentadienyl)zirconium dichloride. The slurry was stirred for 1 hr., filtered, and dried.

Another catalyst, referred to herein as Catalyst C, was prepared employing 0.22 grams of the solid obtained by the methylboroxine treatment of the filtrate. The catalyst preparation was the same, namely, 3 ml of a toluene solution containing 6 milligrams of bis(cyclopentadienyl)zirconium dichloride was added to a 10 ml hexane slurry of the solid. The solids were collected on a filter and dried.

The two catalysts were then evaluated in the polymerization of ethylene using particle form polymerization conditions analogous to those used in Example I and II. The catalysts were both as active as the catalysts produced from the catalysts prepared by merely precipitating the MAO using hexane. There was however significantly less fouling of the reactor with Catalysts B and C than with the catalyst of Example II, i.e. where the catalyst was prepared from the solid MAO obtained by merely contacting the commercial product with a countersolvent.

EXAMPLE IV

A series of experiments were carried out to evaluate the effect of the boroxine level on the yield of the inventive solid methylaluminoxy product. The experiments involved, in each case, the use of 5 ml of a methylaluminoxane obtained from Ethyl Corporation and calculated to have 1.7 moles of aluminoxane units per liter based on evaporating the commercial aluminoxane solution at room temperature under a vacuum and then dividing the weight per liter by 58, the molecular weight of one methyl aluminoxane unit. Each 5 ml portion of the MAO solution had 25 ml of hexane added to it. The slurry was then stirred for 1 hr. Then a known amount of trimethylboroxine was added, in all but one experiment, and the slurry stirred for another hour. The solids were collected on a filter, dried in a dry box, and weighed.

Each of the solids obtained were then used to prepare a catalyst system and evaluated for the particle form polymerization of ethylene. In each catalyst preparation a weighed amount of the aluminoxy solid was slurried in 15 ml of hexane and then a toluene solution of bis(cyclopentadienyl) zirconium dichloride was added. The toluene solution of the metallocene contained about 2 mg of the metallocene per milliliter. In each case, the resulting slurry was stirred, the solids collected on a filter, dried, and weighed.

The catalysts were then evaluated for polymerization activity by polymerizing ethylene under particle form conditions. The conditions involved a total pressure of 450 psi, the partial pressure of the isobutane diluent was 160 psi, and the polymerization was carried out at about 70° C. in 2 liters of the isobutane diluent in the presence of hydrogen. The results of the solid MAO precipitations and the results of the polymerizations using catalysts prepared from those precipitated MAOs are set forth in Table I.

TABLE I

| Run No. | (MeBO)$_3$ gm | Al*/B | Yield Solid MAO, gm | Yield PE, gm | Activity gm PE/gm catalyst hr. |
|---|---|---|---|---|---|
| 1 | 0 | — | 0.130 | 31.3 | 456 |
| 2 | 0.018 | 20 | 0.190 | 41.1 | 382 |
| 3 | 0.024 | 15 | 0.211 | 52.96 | 500 |
| 4 | 0.036 | 10 | 0.408 | 25.2 | 200 |
| 5 | 0.050 | 7.3 | 0.514 | 70.0 | 548 |
| 6 | 0.072 | 5 | 0.51 | 36.2 | 282 |
| 7 | 0.180 | 2 | 0.650 | trace | — |

*Calculated Al in aluminoxy units of aluminoxane.

The data reveals that approximately 100% of the MAO is recovered as a solid when the total aluminum to boron ratio is approximately 7.3/1. All the solids with the exception of that produced in Run 7, yielded active ethylene polymerization catalysts when combined with the metallocene. The activity value is based on the total catalyst system, i.e. the solid catalyst resulting from the combination of the solid aluminoxy product and the metallocene.

EXAMPLE V

A larger scale preparation of the inventive solid aluminoxy product was carried out using a 30 weight percent MAO toluene solution obtained from Schering. In this case, 50 ml of the MAO solution was combined with 200 ml of hexane in a dry box with vigorous stirring. The colorless homogeneous toluene solution turned milky white. The slurry was stirred vigorously for 2 hrs. Then to the above slurry was added dropwise a 50 ml hexane solution of methylboroxine to give 1.4 gm or 33.5 millimoles of methylboroxine. This also translates to calculated aluminum to boron ratio of 7.5 to 1. The complete addition took 1½ hrs. The thick, milky slurry was stirred an additional 3 hrs. and the resulting solid was collected on a filter and dried. A yield of 15.1 gm of solid was obtained which is considered to be about 100% of the MAO in the starting commercial solution.

EXAMPLE VI

In this example, trimethyoxyboroxine rather than methylboroxine was employed as the precipitating agent. In this case, a 10 ml solution of methylaluminoxane in toluene was used that had been obtained from Ethyl Corporation, the methylaluminoxane solution was believed to be 1.7 molar in regard to methylaluminoxane. Here 50 ml of hexane was added to 10 ml of the methylaluminoxane solution. The clouded slurry was stirred for 1 hr. then a 1 ml toluene solution of trimethoxyboroxine containing 0.131 gm of the boroxine was added dropwise to the slurry. The resulting slurry was then stirred for an additional hour at room temperature. The solids were collected on a filter and dried in a dry box. 1 gram of solid dry product was obtained.

Figure 3:
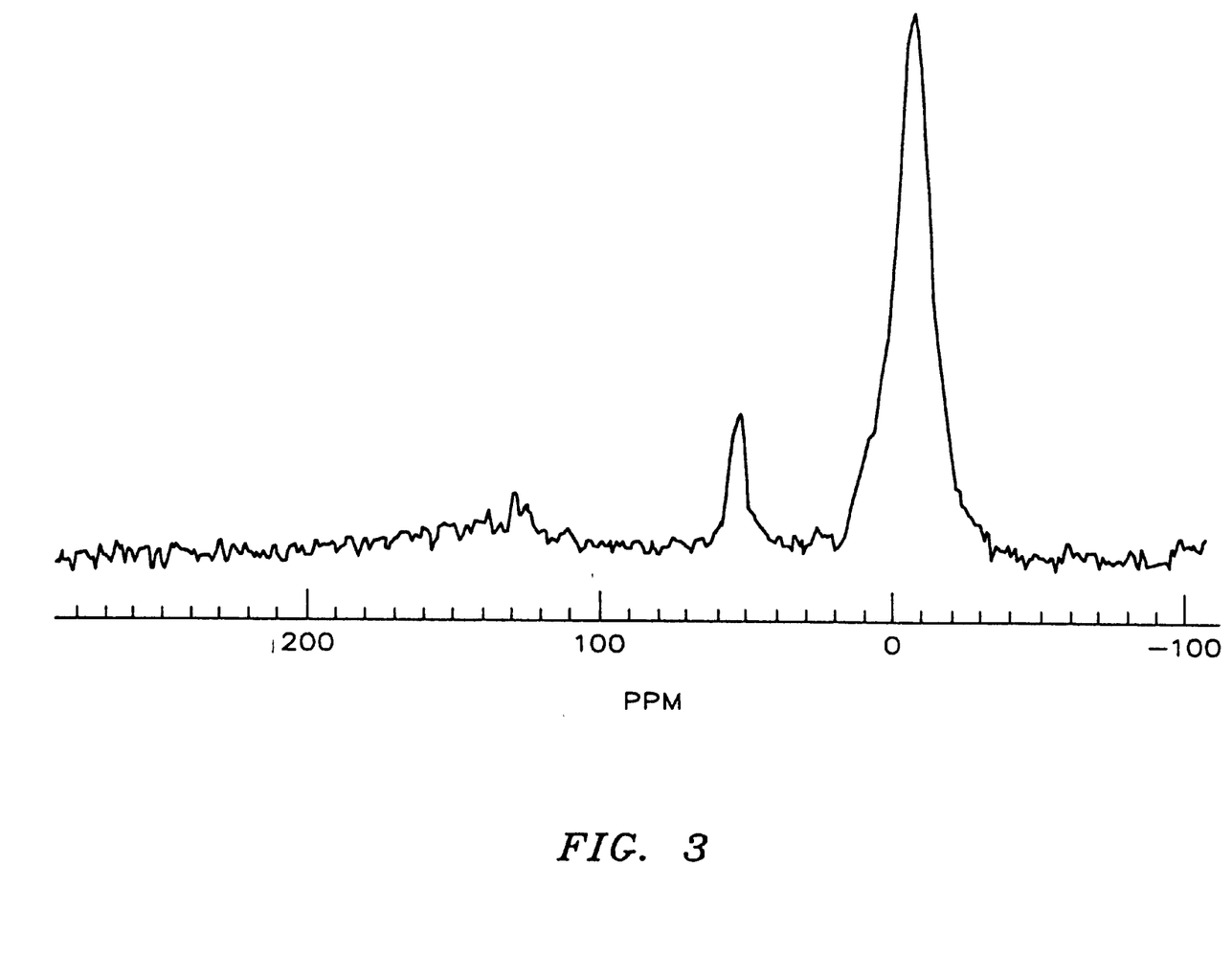
FIG. 3 is a graph showing a $^{13}$C-NMR spectra of the solid resulting from the reaction of a commercial methylaluminoxane with methoxy boroxine.
Figure 4:
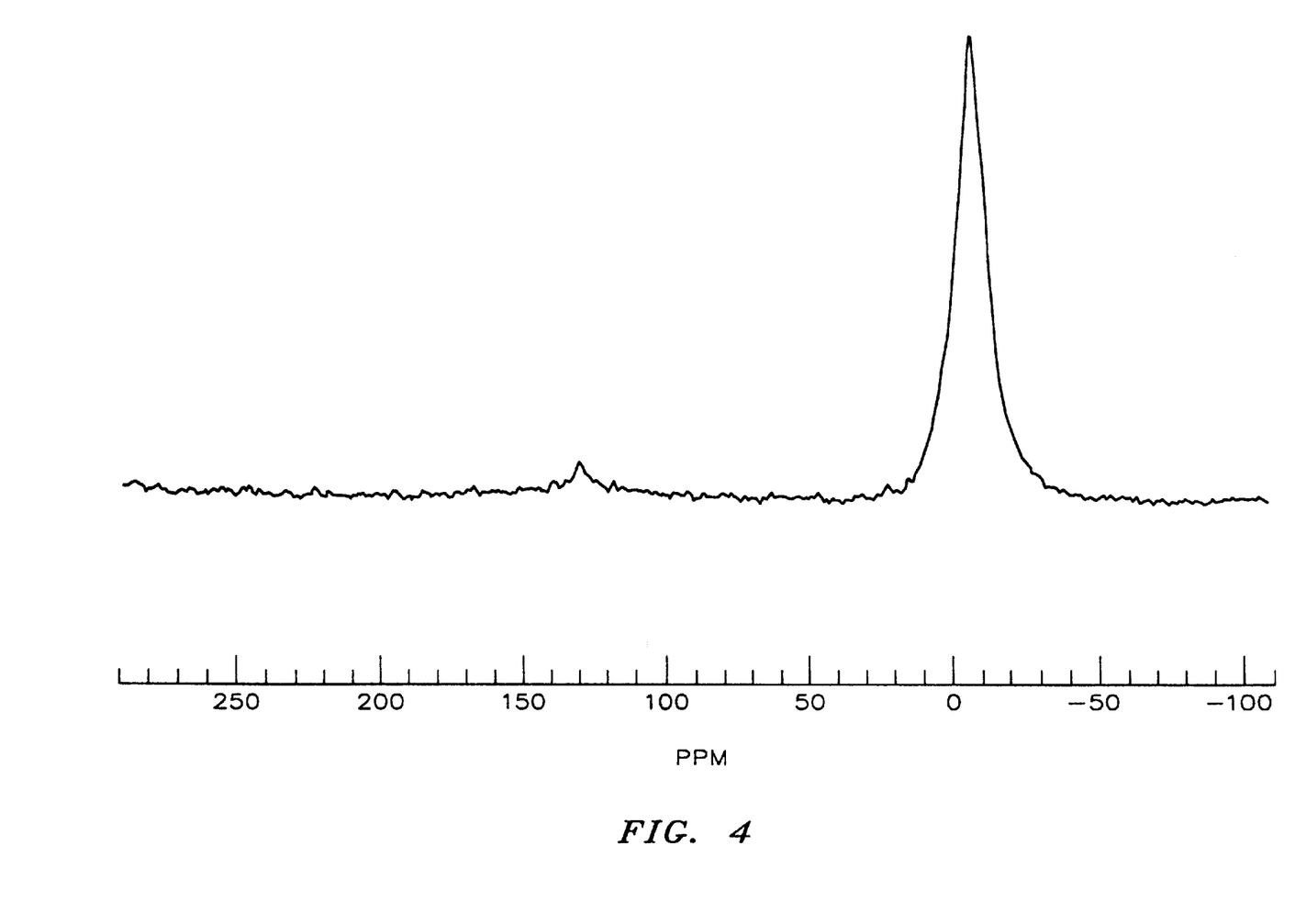
FIG. 4 is a graph showing a $^{13}$C-NMR spectra of the solid resulting from vaccuum stripping a commercial methylaluminoxane solution.

The solid was screened through an 80 mesh sieve and then subjected to MAS NMR analysis using a Bruker/IBM WP200 NMR spectrometer operating at 50.32 MHz for $^{13}$C analysis using a Chemagnetics MAS probe with 7 mm zirconia rotors spinning at 6–7 KHz. Hexamethylbenzene was used as a secondary chemical shift reference to TMS. FIG. 3 shows the resulting $^{13}$C-NMR spectra for the solid obtained using trimethoxyboroxine. The spectra shows that in addition to the broad peak centered at about –8.9 ppm which is due to the MAO, a smaller peak was present at about 51.8 ppm which is attributed to methoxy groups. This spectra indicates that the solid product obtained by using trimethoxyboroxine contains methoxy groups. A $^{13}$C-NMR spectra on the solid resulting from the vaccum stripping of a MAO solution was also made. See FIG. 4. This spectra does not reveal a peak at 51.8 ppm, i.e. the methoxy peak.

A $^{11}$B-NMR spectroanalysis was also carried out using $BPO_4$ as a reference. The $BPO_4$ reference alone has a spectrum containing a relatively narrow line referenced at 0 ppm with spinning sidebands on both sides. The spectrum of the inventive trimethoxyboroxine precipitated aluminoxane contained a broad peak centered about 0 ppm with broad sidebands on both sides. This is certainly evidence that the inventive methoxyboroxine-precipitated aluminoxy product contains boron. This is in contrast to the results obtained using methylboroxine rather than methoxyboroxine. When the $^{11}$B NMR was conducted on methylboroxine precipitated aluminoxane, the spectra did not reveal the presence of a significant amount of boron.

EXAMPLE VII

A series of precipitations were conducted using various levels of trimethoxyboroxine in combination with a methyl aluminoxane obtained from Schering. A 5 ml portion of the Schering MAO was stripped to dryness to yield 0.33 grams of a solid. Considerable volatile trimethylaluminum was seen in the trap. Based upon the weight of the solid recovered, it is calculated that the commercial MAO solution was 1.14 molar in aluminoxy aluminum.

The precipitations were conducted by using a solution of trimethoxyboroxine in toluene. The solution was prepared by dissolving 1 gram of the boroxine in 10 ml of toluene. The precipitation was carried out by adding 25 ml of hexane to 5 ml of the commercial MAO solution. The resulting mixture was then stirred 1 hour, and then a specific volume of a 0.01 g/ml trimethoxyboroxine toluene solution was added, the mixture stirred 3 hours, and then the solid was collected by filtration and dried.

The amounts of trimethoxyboroxine employed in the amount of solid aluminoxane obtained is reported in Table II.

TABLE II

| Run No. | $(MeOBO)_3$, ml | Al*/B | Yield Solid MAO, gm |
|---|---|---|---|
| 8 | 0.327 | 10 | 0.120 |
| 9 | 0.49 | 6.65 | 0.164 |
| 10 | 0.55 | 6.0 | 0.168 |
| 11 | 0.61 | 5.33 | 0.220 |
| 12 | 0.71 | 4.67 | 0.335 |

*Calculated Al in aluminoxy units of aluminoxane.

The activities of the solid aluminoxy product of Runs 11 and 12 were evaluated by slurrying 0.12 grams of the solid aluminoxy product in 25 ml of hexane and then adding a 1 ml toluene solution of 3 mg bis-cyclopentadienyl zirconium dichloride and stirring overnight to obtain a solid catalyst. The solid catalysts were then employed in the polymerization of ethylene using substantially identical conditions. The polymerizations were carried out generally in the manner as described in Example IV. The catalyst system produced using the solid aluminoxane of Run 11 was more active than the catalyst system produced using the solid aluminoxane of Run 12. It is theorized that the solid aluminoxane loses some of its benefits if the level of boroxine is too high. Similar results were noted for the methyl boroxine precipitated aluminoxane in the above Table I.

EXAMPLE VIII

Another series of methoxy boroxine precipitated aluminoxy products was prepared from a 10 wt. % methylaluminoxane solution in toluene obtained from Schering. The procedure involved adding 75 ml of hexane to 10 ml of the commercial MAO solution and stirring for 1 hr. Then a toluene solution of the trimethoxyboroxine was added, when employed. The trimethoxyboroxine solution that was employed was prepared by adding 1 gram of trimethoxyboroxine to 10 ml of toluene. The slurry was then stirred for three more hours and the solids collected and dried. Catalysts were prepared by adding 2 ml of a 3 mg/ml toluene solution of bis-cyclopentadienyl zirconium dichloride to a slurry prepared by adding 0.25 grams of the solid MAO in 30 ml of hexene. The slurries were stirred overnight. The solids were collected on a filter and dried to yield the supported catalyst system.

The catalysts were then each evaluated for their effectiveness in the polymerization of ethylene under comparable conditions. The conditions involved a total pressure of about 341 psi in 2 liters of isobutane. The polymerization was carried out at about 70° C. in the presence of hydrogen. The results of the solid MAO precipitations and the results of the polymerizations using the catalysts prepared from those solid MAOs are set forth in Table III.

TABLE III

| Run No. | $(MeOBO)_3$ mmol | Al*/B | Solid MAO gm | Yield PE, gm | Activity gm PE/gm catalyst |
|---|---|---|---|---|---|
| 13 | 2.5 | 9 | 0.46 | 144.2 | 1419 |
| 14 | 2.8 | 8 | 0.53 | 49.3 | 433 |
| 15 | 2.7 | 8.5 | 0.47 | 19.7 | 1461 |
| 16 | 0 | 0 | 0.25 | 18.93 | 212 |

*Calculated Al in aluminoxy units of aluminoxane.

Here again, it is revealed that the aluminum to boron ratio can affect the activity of the resulting catalyst system.

EXAMPLE IX

A commercial ethyl aluminoxane solution in toluene containing above 10 wt. % ethyl aluminoxane and containing about 31 wt. % aluminum was contacted with a hexane solution of methyl boroxine to produce a solid inventive aluminoxy product. Specifically, 50 ml of the commercial ethyl aluminoxane solution was employed and the methyl boroxine/hexane solution was added dropwise in an amount sufficient to add 0.269 grams of methyl boroxine. The mixture gradually became cloudy. It was allowed to sit and then stirred after complete addition of the boroxine. A slurry of the inventive solid ethyl aluminoxy product resulted. A 5 ml portion of the slurry was combined with 10 ml of a solution of bis n-butylcyclopentadienyl zirconium dichloride containing 4 mg of the metallocene. Approximately half of the resulting slurry was withdrawn by a syringe and used in an ethylene polymerization under particle form polymerization conditions. The catalyst was active. After the resulting polymer was dried, it weighed 104 grams and the polymerization was only carried out for one-half hour.

An attempt was made to carry out the same reaction using the commercial ethyl aluminoxane solution rather than the inventive solid ethyl aluminoxane. The yield of polymer was lower and there was a heavy coating of polymer on all the metal surfaces of the reactor. In contrast, in using the inventive solid ethyl aluminoxane there was only a film of polymer on the reactor walls.

EXAMPLE X

The inventive solid ethyl aluminoxy product prepared in the previous example was combined with 0.048 grams of 1-(9-fluorenyl)-1-cyclopentadienyl methane zirconium dichloride, a sandwich bonded bridged ligand metallocene, dissolved in 5 ml of toluene.

The resulting catalyst system was then evaluated in the homopolymerization of propylene under particle form conditions. The aluminum to zirconium ratio was 1,261. The polymerization was carried out for 60 minutes. The polymerization produced 13,254 grams of polypropylene per gram of metallocene in the hour. The polymer had a melt flow of 89.79, a bulk density of 15.0, a weight average molecular weight of 52,470, a number average molecular weight of 32,2240, a heterogenity index of 1.63, and a density of 0.8931.

A similar propylene polymerization run was carried out using the same metallocene but with the commercial ethyl aluminoxane solution rather than the inventive methyl boroxine precipitated aluminoxy product. Three different aluminum to zirconium ratios were evaluated, namely ratios of 991, 782, and 577. The highest activity obtained in the polymerizations carried out using the commercial ethyl aluminoxane was 2,737 grams of polymer per gram of metallocene.

Similar evaluations were carried out using inventive methyl boroxine precipitated ethyl aluminoxy products in which the ratio of the aluminum to boroxine was 5:1 in one case, 7.75:1 in another case, and 10:1 in yet another case. These inventive solid aluminoxy products were evaluated in the polymerization of propylene by preparing catalysts using the same methane bridged fluorenyl cyclopentadienyl zirconium dichloride sandwich bonded metallocene. The catalyst resulting from the precipitation using the 5:1 ratio was less active than the one prepared using the 7.75:1 ratio which in turn was less active than the one prepared using the 10:1 ratio. The ratio of the Al to the Zr in these runs was in the range of about 850/1 to 980/1.

EXAMPLE XI

A large quantity of trimethoxyboroxine precipitated methyl aluminoxy product was prepared so that the inventive aluminoxy product could be evaluated for ethylene polymerization on a pilot plant scale in a loop reactor. The inventive solid MAO was prepared from a 10 wt. % solution of MAO in toluene obtained from Schering. The procedure employed for preparing large batches involved the following: (1) 6 gallons of hexane was added to a 10 gallon glass-lined reactor. (2) 7.25 lbs. of the commercial 10 wt. % MAO solution was added to the stirred hexanes. (3) The resulting slurry as stirred for 1 hour. (4) 300 ml of a toluene solution containing about 32 grams of trimethoxyboroxane was added over a 1 hr. period with stirring. (5) The resulting slurry was then stirred for an additional 6 hrs. (6) The solids were allowed to settle overnight. (7) About 5 gallons of solvent was decanted. (8) The remaining solids were washed with 1 gallon of hexanes for 1 hr. with stirring. (9) The major portion of the solvent was decanted and the solids were transferred to a carboy for storage. Three such batches were made.

Each of the resulting inventive solid boroxine precipitated aluminoxy products were combined with a hexene solution of bis n-butylcyclopentadienyl zirconium dichloride by adding the metallocene solution to the solid MAO slurry. The resulting slurry was stirred to assure good mixing and the solid allowed to settle and then the solids were transferred to a carboy. The solids were in each case then collected on a filter, dried, and weighed in a drybox. After isolation, each batch of the precipitated metallocene/MAO catalyst system was checked for activity at standard conditions. The catalysts typically contained about 0.3 weight percent zirconium and about 41 weight percent aluminum.

The batches which all proved to be suitably active were then combined to give 225 grams of solid which was sieved through a 60 mesh screen in a drybox. This sieved solid was combined with 1 liter of hexanes and then used in pilot plant scale particle form loop polymerizations of ethylene. The pilot plant process employed a 23 gallon pipe loop reactor, a flash chamber, and polymer fluff dryer. Most of the runs were made at about 194° F. reactor temperature and 13–14 mole percent ethylene in the flash gas. However, in the runs which were made to produce lower density products, the reactor temperature was closer to about 180° F., 1-hexene was used as comonomer, and the ethylene mole percent in the flash gas was about 7 to about 8 mole percent. Typically the residence time in the pilot plant reactor was nominally 1.25 hrs. For each set of conditions, batches of polymer fluff were produced in the loop reactor and combined to produce a blend corresponding to the product resulting from those particular process conditions. Each blend was then extruded into pellets. The reactor was used for a two week period in preparing these polymer batches without any need for stopping for cleaning due to fouling. A summary of some of the properties of the various polymers made using the inventive catalyst system in the pilot plant loop reactor are set forth in Tables IV and V.

TABLE IV

Polymer Physical Properties from Metallocene Catalyst Resins

| Blend | Pellet Values | | Unmilled | Bell ESCR | Flex Mod., |
| | MI | Density | Fluff MI | hrs. | KSI |
| --- | --- | --- | --- | --- | --- |
| 13 | 7.32 | 0.9641 | 11.08 | <24 | 278 |
| 14 | 25.05 | 0.9623 | 28.32 | BOB* | 250 |
| 15 | 43.17 | 0.9624 | 49.91 | <24 | 236 |
| 16 | 18.80 | 0.9504 | 20.49 | BOB | 189 |
| 17 | 32.88 | 0.9502 | 37.21 | BOB | 199 |

TABLE IV-continued

Polymer Physical Properties from Metallocene Catalyst Resins

| Blend | Pellet Values | | Unmilled Fluff MI | Bell ESCR hrs. | Flex Mod., KSI |
|---|---|---|---|---|---|
| | MI | Density | | | |
| 18 | 38.24 | 0.9530 | 39.86 | BOB | 166 |
| 19 | 44.09 | 0.9537 | 44.40 | BOB | 136 |
| 20 | 8.21 | 0.9435 | 8.15 | <24 | 133 |
| 21 | 3.59 | 0.9378 | 3.69 | >1000 | 111 |
| 22 | 3.66 | 0.9330 | 3.82 | >1000 | 87 |

*BOB indicates "breaks-on-bending".

TABLE V

Results of GPC of Metallocene Catalyst Resins

| Blend | MW/MN | IB | MN/1000 | MW/1000 | MZ/1000 |
|---|---|---|---|---|---|
| 13 | 21.1 | 1.284 | 10.5 | 220 | 4375 |
| 14 | 16.7 | 1.234 | 9.7 | 162 | 4202 |
| 15 | 13.3 | 1.222 | 8.3 | 111 | 3602 |
| 16 | 11.5 | 1.089 | 11.2 | 128 | 19,572 |
| 17 | 8.6 | 1.105 | 9.7 | 83 | 2866 |
| 18 | 11.2 | 1.131 | 9.2 | 103 | 6092 |
| 19 | 8.1 | 1.129 | 8.8 | 71 | 2803 |
| 20 | 3.9 | 0.993 | 16.0 | 63 | 966 |
| 21 | 3.3 | 0.972 | 20.0 | 67 | 142 |
| 22 | 4.2 | 0.968 | 18.0 | 76 | 822 |

Blend 13 was the product of ethylene bomopolymerization. The subsequent blends 14–22 were the products of copolymerizations which employed 1-hexene as a comonomer with the ethylene. A difference in the ratios of the weight average molecular weight to number average molecular weight, i.e. MW/MN, was observed to be due to the fact that in the polymers having a higher ratio there was a significant tail on the high molecular weight end of the molecular weight distribution. The presence of this tail seems to be a function of the reactor conditions used to produce the various resins, particularly the amount of comonomer employed. Catalyst productivities determined from total burned ash were in the range of 3,664 to 8,793 lbs. of polymer per pound of catalyst were noted, where catalyst refers to the solid catalyst system resulting from the combination of the metallocene and the inventive solid aluminoxy product.

We claim:

1. A process for producing a polymer comprising contacting at least one olefin under suitable polymerization conditions with a catalyst system comprising at least one transition metal-containing olefin polymerization catalyst and a solid co-catalyst produced by contacting a solution of an organo aluminoxane having aluminoxy units of the formula wherein R is a hydrocarbyl group, with an organo boroxine, wherein the molar ratio of the boron in the organo boroxine to aluminum in the aluminoxy units of the aluminoxane is in the range of about 1:20 to about 1:3.

2. A process according to claim 1, wherein a solution comprising methylaluminoxane and trimethylaluminum is contacted with a countersolvent to result in n slurry containing solid methylaluminoxane and then said slurry is contacted with methylboroxine to produce said solid cocatalyst.

3. A process according to claim 1, wherein said organoboroxine consists essentially of methoxyboroxine.

4. A process according to claim 1, wherein said polymerization is conducted under particle form conditions.

5. A process according to claim 4, which is conducted in a continuous loop reactor.

6. A process according to claim 5, wherein said solid cocatalyst product is produced by reacting trimethoxyboroxine with an alkylaluminoxane.

7. A process according to claim 6, wherein said olefin polymerization catalyst comprises bis(n-butyl cyclopentadienyl)zirconium dichloride.

8. A process according to claim 5, wherein said solid cocatalyst is prepared by reacting trimethoxyboroxine with methyl aluminoxane.

9. A process according to claim 8, wherein said olefin consists essentially of ethylene, said polymerization is conducted in the presence of hydrogen and the polymer produced has a molecular weight distribution such that the weight average molecular weight divided by the number average molecular weight is in the range of 10 to 21.

10. A process according to claim 1, wherein said solid cocatalyst is prepared using methyl aluminoxane and said olefin polymerization catalyst comprises a metallocene.

11. A process according to claim 1 wherein the atomic ratio of aluminum in the solid cocatalyst to the transition metal of said catalyst is in the range of about 1/1 to about 5000/1.

12. A process according to claim 1 wherein said organoboroxine consists essentially of methylboroxine.

13. A process according to claim 1 wherein said solid cocatalyst is prepared using ethylaluminoxane and said olefin polymerization catalyst comprises a metallocene.

14. A process according to claim 13, wherein propylene is homopolymerized and said metallocene comprises 1-(9-fluorenyl)-1-(cyclopentadienyl)-methane zirconium dichloride.

15. A process for producing a polyethylene under particle form conditions in a continuous loop reactor with a single transition metal catalyst so that the polyolefin has a molecular weight distribution wherein the ratio of the weight average molecular weight to the number average molecular weight is in the range of 10 to 21, said process comprising carrying out the reaction in the presence of a catalyst system consisting essentially of a metallocene and a solid having aluminoxy units, said solid being substantially insoluble in the polymerization diluent at the polymerization conditions.

* * * * *